(12) United States Patent　(10) Patent No.: US 7,957,783 B2
Atalar et al.　(45) Date of Patent: Jun. 7, 2011

(54) ELECTRICAL LEAD FOR AN ELECTRONIC DEVICE SUCH AS AN IMPLANTABLE DEVICE

(75) Inventors: Ergin Atalar, Columbia, MD (US); Onur Ferhanoglu, Istanbul (TK)

(73) Assignees: Boston Scientific Neuromedulation Corporation, Valencia, CA (US); Surgivision, Inc., Memphis, TN (US)

( * ) Notice: Subject to any disclaimer, the term of this patent is extended or adjusted under 35 U.S.C. 154(b) by 0 days.

(21) Appl. No.: 12/478,145

(22) Filed: Jun. 4, 2009

(65) Prior Publication Data

US 2009/0254152 A1　Oct. 8, 2009

Related U.S. Application Data

(62) Division of application No. 11/417,594, filed on May 4, 2006, now Pat. No. 7,561,906.

(60) Provisional application No. 60/677,418, filed on May 4, 2005.

(51) Int. Cl.
*A61B 5/04* (2006.01)

(52) U.S. Cl. ........................................ 600/374; 607/116

(58) Field of Classification Search .................. 607/116; 600/374
See application file for complete search history.

(56) References Cited

U.S. PATENT DOCUMENTS

| | | | |
|---|---|---|---|
| 2,130,758 A | 9/1938 | Rose | 607/155 |
| 3,218,638 A | 11/1965 | Honig | 342/50 |
| 4,766,381 A | 8/1988 | Conturo et al. | |
| 5,246,438 A * | 9/1993 | Langberg | 606/33 |
| 5,281,914 A | 1/1994 | Conturo et al. | |
| 5,314,458 A | 5/1994 | Najafi et al. | 607/116 |
| 5,352,979 A | 10/1994 | Conturo | |
| 5,370,644 A | 12/1994 | Langberg | 606/33 |
| 6,188,219 B1 | 2/2001 | Reeder et al. | |
| 6,284,971 B1 | 9/2001 | Atalar et al. | |
| 6,408,202 B1 | 6/2002 | Lima et al. | |
| 6,944,489 B2 | 9/2005 | Zeijlemaker et al. | |
| 6,980,863 B2 | 12/2005 | Van Venrooij et al. | |
| 6,985,775 B2 | 1/2006 | Reinke et al. | |
| 7,013,180 B2 | 3/2006 | Villaseca et al. | |
| 7,015,393 B2 | 3/2006 | Welner et al. | |
| 7,561,906 B2 * | 7/2009 | Atalar et al. | 600/374 |
| 2004/0263174 A1 | 12/2004 | Gray et al. | 324/322 |

OTHER PUBLICATIONS

International Search Report and Written opinion for PCT/US06/17362, International Filing Date May 4, 2006, Date of Mailing Aug. 12, 2008.

* cited by examiner

*Primary Examiner* — Carl H. Layno
*Assistant Examiner* — Jon-Eric C. Morales
(74) *Attorney, Agent, or Firm* — Frommer Lawrence & Haug LLP; Bruce E. Black

(57) ABSTRACT

A lead for an electronic device which resists the induction of a current from an electromagnetic field external to said lead includes one or more pairs of adjacent segments of electrical wire, each of the pairs including a first segment of electrical wire and a second segment of electrical wire. The lead also includes one or more shielded RF chokes, wherein each of the shielded RF chokes is provided between the first segment of electrical wire and the second segment of electrical wire of a respective one of the one or more pairs of adjacent segments. Also, an implantable device that includes a generator for generating one or more electrical pulse and a lead as described for delivering the pulses to tissue within a patient's body. A method for making the described implantable device is also provided.

32 Claims, 12 Drawing Sheets

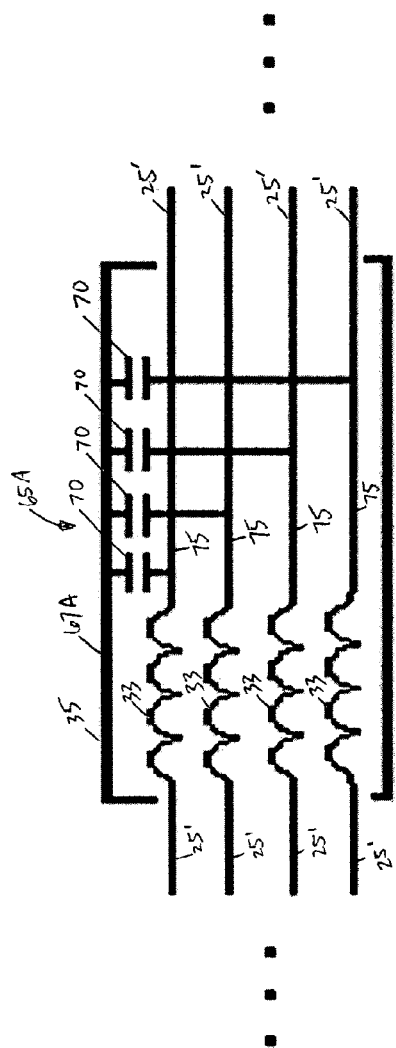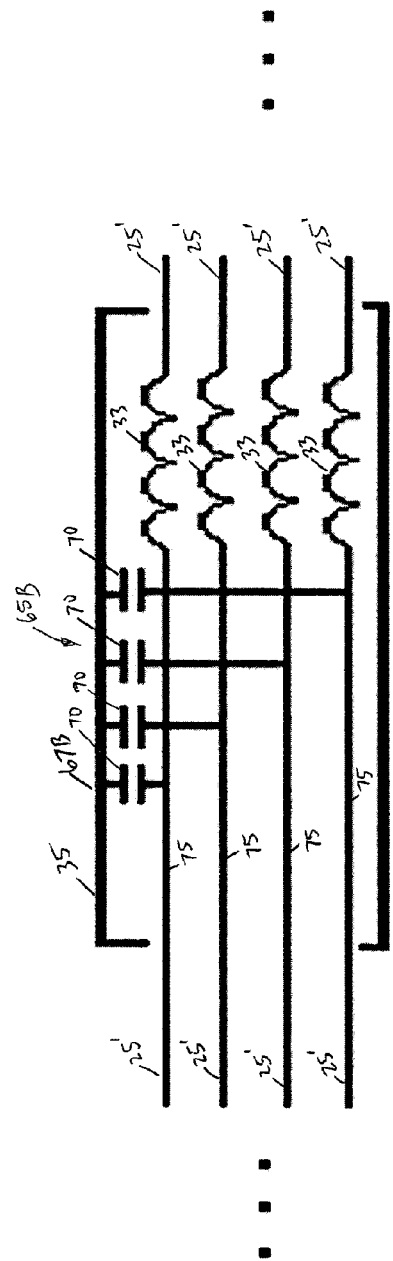

ELECTRICAL LEAD FOR AN ELECTRONIC DEVICE SUCH AS AN IMPLANTABLE DEVICE

CROSS-REFERENCE TO RELATED APPLICATION

This application is a division of U.S. patent application Ser. No. 11/417,594, filed May 4, 2006, now U.S. Pat. No. 7,561, 906, which claims the benefit of U.S. Provisional Patent Application No. 60/677,418, entitled "MRI Compatible Implantable Devices," which was filed on May 4, 2005, the disclosures of which are incorporated herein by reference.

FIELD OF THE INVENTION

The present invention relates to electrical leads for devices such as, without limitation, implantable devices, and in particular to an electrical lead which resists the induction of currents from an external electromagnetic field and therefore reduces the likelihood of excessive heating from such fields.

BACKGROUND OF THE INVENTION

Magnetic resonance imaging (MRI) is generally regarded as an extremely safe, non invasive diagnostic technique. MRI may, however, pose a threat to patients that have implantable devices, such as, without limitation, a deep brain stimulation (DBS) device, a pacemaker, a neurostimulator, or a cardio defibrillator. Currently, patients with metallic implants are not allowed to undergo an MRI scan. One of the main reasons for this is the excessive heating caused by the electromagnetic field concentration around the leads of an implant during an MRI procedure.

Many cases with substantial temperature increase during MRI scanning have been reported and reviewed. For example, in Achenbach S, Moshage W, Diem B, Bieberle T, Schibgilla V, Bachmann K., "Effects of Magnetic Resonance Imaging on Cardiac Pacemakers and Electrodes," Am Heart J 1997; 134:467-473, a maximum temperature increase of 63.1° C. was reported during 90 seconds of MRI scanning. Additionally, in an in vitro evaluation of 44 commercially available pacemaker leads, it was reported in Sommer T, Hahlhaus C, Lauck G, et al., "MR Imaging and Cardiac Pacemakers: In Vitro Evaluation and In Vivo Studies in 51 patients at 0.5 T.," Radiology 2000; 215:869-879, that a temperature increase of 23.5° C. was observed in a 0.5 Tesla experiment. Substantial temperature increases were also observed in MRI scans involving patients with neurostimulators, as reported in Gleason C A, Kaula N F, Hricak H, et al., "The Effect of Magnetic Resonance Imagers on Neurostimulators," Pacing Clin Electrophysiology 1992:15; 81-94. Furthermore, 1.5 T and a SAR of 3.0 W/kg have been shown to cause severe necrosis in the mucous membranes of dogs with transesophageal cardiac pacing leads as reported in Hofman M B, de Cock C C, van der Linden J C, et al., "Transesophageal Cardiac Pacing During Magnetic Resonance Imaging: Feasibility And Safety Considerations," Magn Reson Med 1996; 35:413-422.

Moreover, a 16.8° C. temperature increase on a half wavelength wire in a gel-phantom experiment was observed and reported in Smith C D, Kildishev A V, Nyenhuis J A, Foster K S, Bourland J D, "Interactions Of MRI Magnetic Fields With Elongated Medical Implants," J Applied Physics 2000; 87:6188-6190. As reported in Konings M K, Bartels L W, Smits H J, Bakker C J, "Heating Around Intravascular Guidewires By Resonating RF Waves," J Magn Reson Imaging 2000; 12:79-85, temperature increases due to endavascular guidewires between 26° C. and 74° C. were observed in saline bath experiments of up to 30 seconds of scan time. In another experiment with saline solution, reported in Nitz W R, Oppelt A, Renz W, Manke C, Lenhart M, Link J., "On The Heating Of Linear Conductive Structures As Guide Wires And Catheters In Interventional MRI," J Magn Reson Imaging 2001; 13:105-114, up to 34° C. of temperature increase was observed for a half wavelength wire. It should be noted that first, second or third order burns were observed in many of the in-vivo studies mentioned above.

A recent study was performed for one of the most widely used neurostimulation systems, the Activa Tremor Control System sold by Medtronic. Different configurations were evaluated to assess worst case and clinically relevant positioning scenarios, and in vitro experiments were performed at 64 MHz MR system using gel phantoms to represent human tissue. As reported in Rezai A R, Finelli D, Nyenhuis J A, et al., "Neurostimulator For Deep Brain Stimulation: Ex Vivo Evaluation Of MRI-Related Heating At 1.5-Tesla," J Magn Reson Imaging 2002:15:241-250, the highest temperature change observed was 25.3° C. for the RF coil and 7.1° C. for the head coil. These results indicate that heating may be hazardous under certain MRI scanning conditions.

The FREEHAND System Implantable Functional Neurostimulator is a commercially available RF-powered motor control neuroprosthesis that consists of both implanted and external components sold by NeuroControl Corporation of Cleveland, Ohio. Findings from of an MRI-induced heating experiment during which the FREEHAND System was exposed to a whole-body-averaged SAR of 1.1 W/kg for 30 minutes showed that localized temperature increases were no greater than 2.7° C. with the device in a gel-filled phantom. A patient with a FREEHAND system can thus only undergo an MRI procedure under certain input power levels for a 1.5 Tesla scanner.

Due to the safety concerns created by the potential for excessive heating as described above, several strategies have been developed to promote MRI safety for patient's having metallic implants. One of the basic ones is to set a power threshold that ensures only a reasonable amount of heating will occur. A methodology for such a power limitation was previously published in Yeung C J, Susil R C, Atalar E., "RF Safety Of Wires In Interventional MRI: Using A Safety Index," Magn Reson Med 2002; 47:187-193. However, many modern MRI pulse sequences, such as fast spin-echo or steady-state free precession (SSFP), require high RF power levels and therefore there is no guarantee that good quality images can be acquired if RF power is limited.

Most of the studies on the heating of metallic implants concentrate on the heating of the leads of the implant rather than the generator of the implant. This is primarily due to the fact that generators are typically smooth devices with curved edges and are therefore less threatening structures than the leads in terms of electromagnetic field concentration. As a result, less heating is observed and smaller temperature increase is expected in generators. See, for example, the results reported in Ferhanoglu O, Tasci O. T, El-Sharkawy A, Altintas A, Atalar E, "Investigating RF Heating Of Pacemakers In MRI Using A Safety Index", Proc. International Society of Magnetic Resonance in Medicine, 12th Scientific Meeting, Kyoto, 2004, and Ferhanoglu O, El-Sharkawy A, Atalar E, "RF Heating At The Tip Of Pacemaker Leads," Proc. European Society of Magnetic Resonance in Medicine and Biology, 21st Scientific Meeting, Copenhagen, 2004.

U.S. Pat. No. 6,284,971 discloses a coaxial cable which may be a magnetic resonance imaging coaxial cable designed for enhanced safety so as to reduce the risk of excessive heating or burns to a user. The cable has an elongated axially oriented inner conductor and an axially oriented outer shield conductor in spaced relationship with respect thereto with a first dielectric material disposed therebetween. However in this design, high permittivity materials must be employed. This requirement may create flexibility problems since high permittivity materials are brittle and rigid. In addition, there may be more than one the lead which may require usage of separate coaxial cables. In such a case, miniaturization of the design is a difficult task.

RF chokes and filters have been used in several previous studies. For example, as described in Susil R C, et al., "Multifunctional Interventional Devices for MRI: A Combined Electrophysiology/MRI Catheter", MRM 47:594-600 (2002), RF chokes were used in the design of a combined electrophysiology/MRI catheter, and as described in Ladd M E, et. al., "Reduction of Resonant RF Heating in Intravascular Catheters Using Coaxial Chokes", MRM 43:615-619 (2000), triaxial chokes were used to present a high impedance to currents flowing on the outer surface of the triax.

U.S. Pat. No. 6,539,253 discloses an implantable medical device incorporating integrated circuit notch filters, and U.S. Pat. No. 5,817,136 discloses a pacemaker with EMI protection. Both of the designs ensure electromagnetic interference is not a problem, however safety in terms of heating is not guaranteed. High current may still be flowing through long cables and these high currents may cause excessive heating and buns.

U.S. Pat. No. 5,217,010 describes optical signal transmission in between the generator and the organ in a pacemaker, which provides safety since there is no coupling with the optical system and the electromagnetic field. However, the electrical to optical and optical to electrical energy conversion efficiency is limited and therefore the lifetime of the pulse generator is reduced significantly. Miniaturization in this case is also a difficult task.

It is thus apparent that a need exists for an electrical lead which may be used with, for example, metallic implants, which resists the induction of currents from an external electromagnetic field, such as the field that is present during MRI scanning, and therefore reduces the likelihood of excessive heating from such fields.

SUMMARY OF THE INVENTION

In one embodiment, the invention relates to lead for an electronic device which resists the induction of a current from an electromagnetic field external to the lead, as may be present during an MRI process. The lead includes one or more pairs of adjacent segments of electrical wire, each of the pairs including a first segment of electrical wire and a second segment of electrical wire. The adjacent segments of electrical wire may be single conductor electrical wires or multiple conductor electrical wires. The lead also includes one or more shielded RF chokes, wherein each of the shielded RF chokes is provided between the first segment of electrical wire and the second segment of electrical wire of a respective one of the one or more pairs of adjacent segments. The shielded RF chokes have a first end operatively coupled to the first segment of electrical wire and a second end operatively coupled to the second segment of electrical wire of the respective pair of adjacent segments. Preferably, the one or more pairs of adjacent segments comprises a plurality of pairs of adjacent segments of electrical wire and the one or more shielded RF chokes comprises a plurality of shielded RF chokes.

In one particular embodiment, the electromagnetic field includes electromagnetic energy having a first wavelength, and the first segment of electrical wire and the second segment of electrical wire in each of the plurality of pairs of adjacent segments of electrical wire each has a length of no more than about a predetermined percentage, such as twenty five percent, of the first wavelength. The electronic device may be a device carried by the body of a patient, such as an implantable device.

The shielded RF chokes may include an inductor covered by one or more layers of conductive shielding material, such as a metallic shielding material. Preferably, a first end of the one or more layers of conductive shielding material is electrically connected to the inductor and a second end of the one or more layers of conductive shielding material is either floating or connected to an insulator. In addition, each inductor in the shielded RF chokes may include a core, such as a paramagnetic core. Alternatively, the shielded RF chokes may comprise toroidal inductors, wherein a coil is wrapped around a doughnut-shaped core. Additionally, one or more electrical shielding layers, such as metallic layers, may be provided around the toroidal inductor to provide additional shielding.

In another embodiment, the lead may further include a layer of insulating material covering at least a portion of the one or more pairs of adjacent segments of electrical wire and at least a portion the one or more shielded RF chokes.

In one particular embodiment, one or more of the one or more shielded RF chokes comprises a first conductor and a first inductor connected in series and provided between the first segment of electrical wire and the second segment of electrical wire of the respective one of the one or more pairs of adjacent segments, at least one layer of conductive shielding material covering the first conductor and the first inductor, and a capacitor provided between the first conductor and the at least one layer of conductive shielding material.

In yet another embodiment, the invention relates to an apparatus that may be implanted within a patient's body which resists the induction of a current from an electromagnetic field external to the apparatus. The apparatus includes a generator for generating one or more electrical pulses, and a lead for delivering the one or more electrical pulses to tissue within the patient's body. The lead in the apparatus may be structured according to the various embodiments described above.

In still a further embodiment, the invention relates to a method of making an implantable device including the various embodiments of the lead described above. In particular, the method includes providing one or more pairs of adjacent segments of electrical wire, each of the pairs including a first segment of electrical wire and a second segment of electrical wire, and providing a shielded RF choke, as described in the various embodiments above, between the first segment of electrical wire and the second segment of electrical wire of each one of the one or more pairs of adjacent segments.

BRIEF DESCRIPTION OF THE DRAWINGS

The accompanying drawings illustrate presently preferred embodiments of the invention, and together with the general description given above and the detailed description given below, serve to explain the principles of the invention. As shown throughout the drawings, like reference numerals designate like or corresponding parts.

FIGS. 3 through 10 are schematic diagrams of various alternative embodiments of an electrical lead according to the present invention;

DESCRIPTION OF THE PREFERRED EMBODIMENTS

Figure 1:
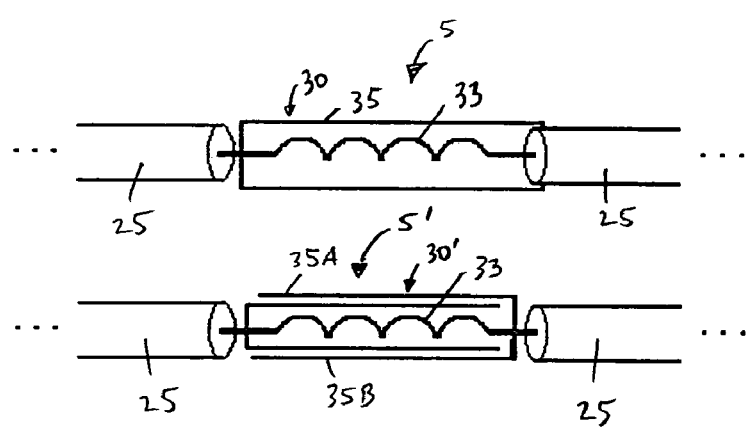
FIG. 1 is a schematic diagram of an electrical lead according to a first embodiment of the present invention.
Figure 2:
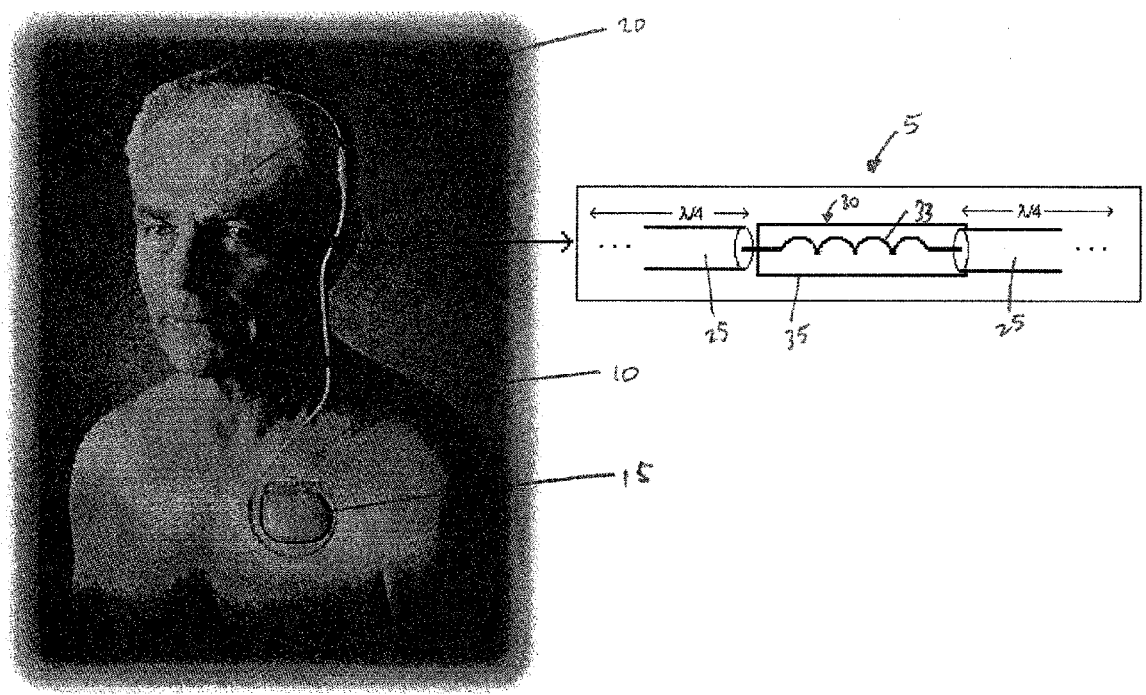
FIG. 2 is a schematic diagram showing the electrical lead of FIG. 1 being used in an implantable device.

FIG. 1 is a schematic diagram of an electrical lead 5 for an electronic device carried by the body of a patient according to a first embodiment of the present invention. As used herein, the term "patient" shall refer to any member of the animal kingdom, including human beings. As used herein, the terms "carried by the body of the patient" in reference to as device shall mean that the device may be implanted within the patient body, worn on or attached externally to the patent's body, or some combination thereof. In the preferred embodiment, as shown schematically in FIG. 2, the electrical lead 5 shown in FIG. 1 forms a part of an implantable device 10, such as, without limitation, a deep brain stimulation (DBS) device, a pacemaker, a neurostimulator, or a cardio defibrillator, to deliver electrical signals (e.g., electrical pulses) from a generator 15 to a location 20, such as an organ or some other tissue, within the body to which the electrical signals are to be applied (for illustrative purposes, FIG. 2 shows a DBS device). As described in greater detail herein, the electrical lead 5 allows for safer MRI scanning of patients by decreasing the amount of heating caused by the RF field.

Referring again to FIG. 1, the electrical lead 5 includes a plurality of segments of electrical wire 25 which, in this embodiment, each comprise a single conductor wire. Preferably, each of the segments of electrical wire 25 comprises a flexible insulated single conductor wire. As seen in FIG. 1, the electrical lead 5 includes a shielded RF choke 30 that is inserted between two adjacent segments of electrical wire 25. As used herein, the term "shielded RF choke" shall refer to an inductor that traps an electromagnetic field or fields within a confined area in order to resist the penetration of external electromagnetic fields into the confined area and therefore resist interaction between external electromagnetic fields and with electromagnetic fields that may exist in the confined area.

In the embodiment shown in FIG. 1, the shielded RF choke 30 comprises an inductor 33, in the form of a coil, surrounded by a layer of electrical shielding material 35, such as a metallic shielding material like copper, aluminum, gold, silver or nitinol. The layer of shielding material 35 helps to reduce the risk of magnetic coupling during an MRI scanning process. As seen in FIG. 1, a first end of the inductor 33 is electrically coupled to one of the adjacent segments of electrical wire 25 and the opposite end of the inductor 33 is electrically coupled to the other of the adjacent segments of electrical wire 25. In addition, one end of the layer of conductive shielding material 35 is electrically connected to the inductor 33 and the other end of the layer of conductive shielding material 35 either floats or touches the insulating material, if present, surrounding the electrical wire 25.

Although only two adjacent segments of electrical wire 25 and one shielded RF choke 30 are shown in FIGS. 1 and 2, it should be understood that the electrical lead 5 may include multiple adjacent segments of electrical wire 25 and multiple shielded RF chokes 30 connected as shown in FIG. 1 and described above. In fact, in the preferred embodiment of the electrical lead 5, the electrical lead 5 includes a length consisting of multiple adjacent segments of electrical wire 25 and multiple shielded RF chokes 30 provided therebetween. In this preferred embodiment, each segment of electrical wire 25 is substantially shorter than one half of the wavelength of the electromagnetic field with which it is desired to use the electrical lead 5. As will be appreciated, if multiple electromagnetic fields are possible, then the shortest of the wavelengths is chosen for this design parameter. In the most preferred embodiment, each segment of electrical wire 25 is less than or equal to about one quarter of the wavelength ($\lambda/4$) of the electromagnetic field (e.g., the RF field to be used in an MRI scanning process; the most common frequency used in MRI scanning are 64 MHz, although 42 MHz and 128 MHz systems are also common) with which it is desired to use the electrical lead 5. In one embodiment, the preferred electrical lead 5 may be a conventional lead used for implantable devices that is serially modified to include the shielded RF chokes 30 at predetermined intervals such as intervals of at least every $\lambda/4$. Alternatively, in another embodiment, the preferred electrical lead 5 may be specially manufactured to include the shielded RF chokes 30 at predetermined intervals such as intervals of at least every $\lambda/4$.

As is known in the art, RF chokes resist the flow of currents of certain frequencies and pass currents of certain relatively lower frequencies (the term "RF trap" is also commonly used). Thus, in the electrical lead 5, the shielded RF choke or chokes 30 will resist (and possibly entirely prevent) current flow at high frequencies such as the RF field frequencies of an MRI device, and will at the same time let the current pass at lower frequencies, e.g., the frequencies of the implantable device with which it is used. As a result, the possibility of the induction of current, and therefore production of heat, due to the RF field of the MRI is reduced (and possibly entirely prevented), while still allowing the transmission of signals from a generator 15 to a location 20 as shown in FIG. 2. In the preferred embodiment, the segment of electrical wire 25 that is provided inside the location 20, such as an organ or other tissue, does not include a shielded RF choke 30, and instead is preferably shorter than $\lambda/2$ and therefore relatively safe.

FIG. 3 is a schematic diagram of an electrical lead 5' according to an alternate embodiment of the present invention that is similar to the electrical lead 5 except that it includes one or more shielded RF chokes 30' that, instead of using a single layer of shielding material 35, employ multiple layers of shielding material 35A and 35B for improved decoupling of the magnetic field. Preferably, the electrical lead 5' includes multiple RF chokes 30 spaced at intervals as described. As seen in FIG. 3, in each layer of shielding material 35A and 35B, one end of the layer is electrically connected to the inductor 33 and the other end of the layer either floats or touches the insulating material, if present, surrounding the electrical wire 25.

Figure 4:
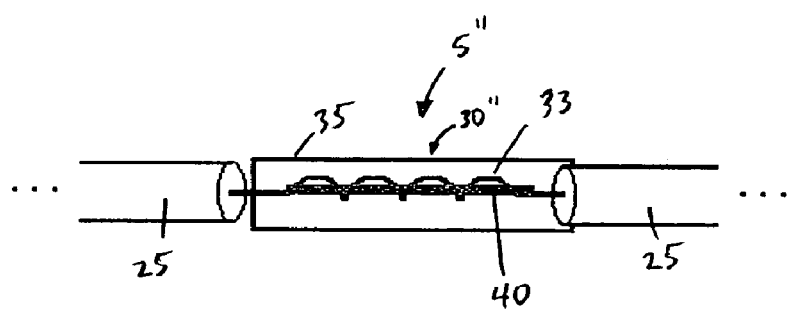

FIG. 4 is a schematic diagram of an electrical lead 5" according to a third, further alternate embodiment of the present invention that is similar to the electrical lead 5 except that it includes one or more shielded RF chokes 30" in the form of inductors 33\that each have a core 40 provided within the inductor 33. The core 40 inside each inductor 33 provides a higher inductance for a given resistance. Preferably, a paramagnetic material, such as, without limitation, aluminum or various plastic materials, is used to form the core 40. Preferably, ferromagnetic materials should not be used for the core 40 to resist any attraction by the magnetic filed of the MRI.

Figure 5:
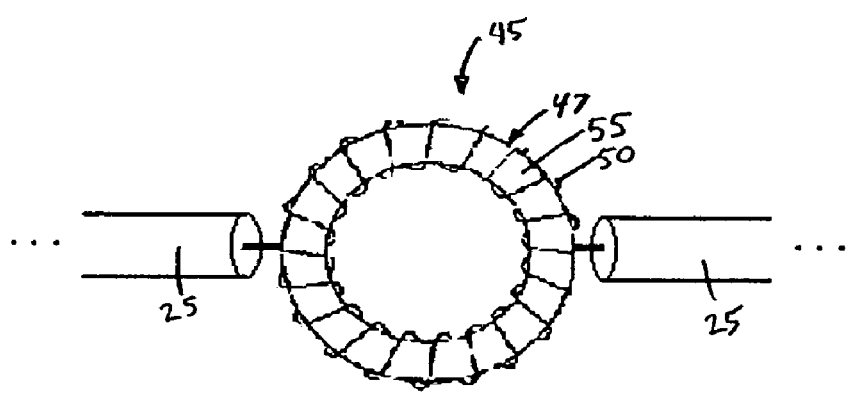

FIG. 5 is a schematic diagram of an electrical lead 45 according to a yet another alternate embodiment of the present invention. The electrical lead 45 is similar to the electrical lead 5 shown in FIG. 1 in that it includes a plurality of segments of electrical wire 25. The electrical lead 45 in this embodiment includes one or more shielded RF chokes 47 each having the form of a toroidal inductor that preferably includes a torus-shaped coil 50 wrapped around a doughnut-shaped core 55. The shielded RF chokes 47 perform essentially the same function as the shielded RF chokes 30 described above as the shielded RF chokes 47 trap electromagnetic fields within the doughnut-shaped core 55 and resist the induction of currents as a result of external electromagnetic fields. Preferably, the electrical lead 45 includes multiple shielded RF chokes 47 spaced at intervals as described above in connection with the shielded RF chokes 30. When the shielded RF chokes 47 are used, there may be no need for a layer of shielding material (as in the shielded RF chokes 30, 30' and 30") as the electromagnetic field is trapped inside the core 55.

Figure 6A:
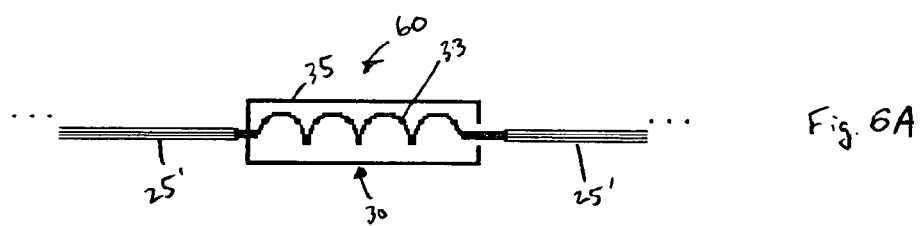
Figure 6B:
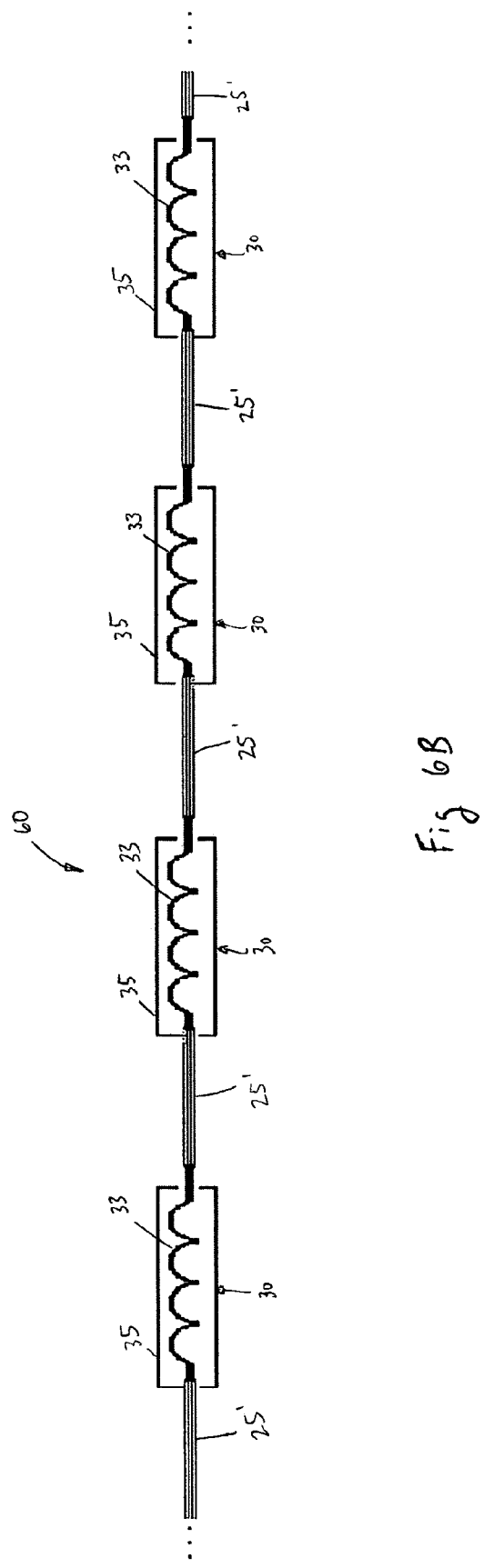

FIG. 6A is a schematic diagram of an electrical lead 60 according to still a further alternate embodiment of the present invention. The electrical lead 60 includes a plurality of segments of electrical wire 25' which, in this embodiment, each comprise a multiple conductor wire, preferably in the form of a flexible insulated multiple conductor wire or a coaxial cable. The electrical lead 60 is similar to the electrical lead 5 shown in FIG. 1 as it includes a one or more shielded RF chokes 30 including an inductor 33 surrounded by layer of shielding material 35 as described above. Preferably, as shown in FIG. 6B, the electrical lead 60 includes multiple shielded RF chokes 30 spaced at intervals as described above in connection with FIG. 1. As seen in FIGS. 6A and 6B, a first end of each inductor 33 of each shielded RF choke 30 is electrically coupled to each of the wires of one of the adjacent segments of electrical wire 25' and the opposite end of the inductor 33 of each shielded RF choke 30 is electrically coupled to each of the wires of the other of the adjacent segments of electrical wire 25'. In addition, it should be appreciated that, in variations of this embodiment, an additional layer or layers of shielding material may be provided as shown in FIG. 3, a core 40 may be provided in the shielded RF choke 30 as shown in FIG. 4, and/or a toroidal RF choke 47 as shown in FIG. 5 may be used.

Figure 7:
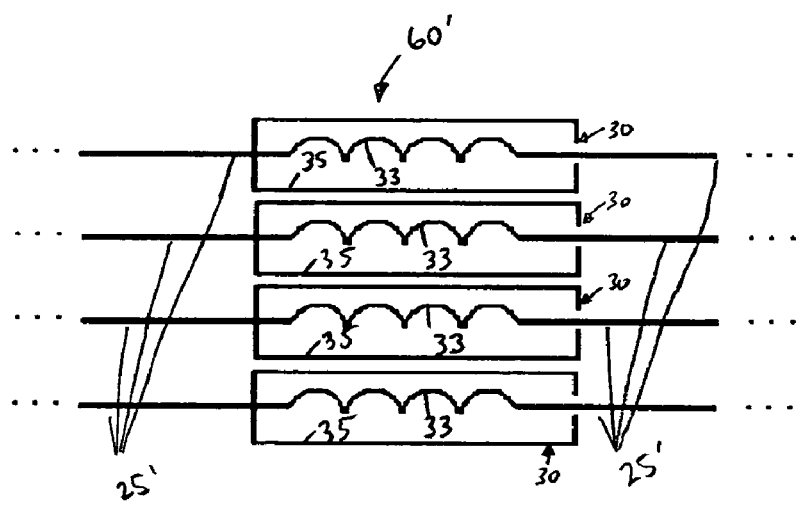
Figure 8:
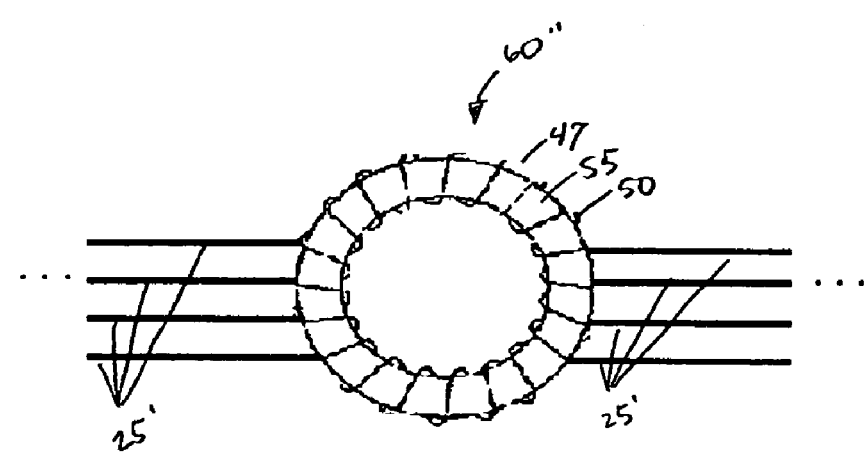

FIG. 7 is a schematic diagram of an electrical lead 60' according to another alternate embodiment of the present invention that is similar to the electrical lead 60 shown in FIG. 6. The electrical lead 60' differs from the electrical lead 60 in that, instead of a single shielded RF choke 30 being provided between adjacent segments of electrical wire 25', multiple shielded RF chokes 30 are provided between adjacent segments of electrical wire 25'. Specifically, as shown in FIG. 7, one shielded RF choke 30 is provided for each conductor contained in the segments of electrical wire 25'. FIG. 8 is a schematic diagram of an electrical lead 60" according to yet another alternate embodiment of the present invention that is similar to the electrical lead 60 shown in FIG. 6 except that each shielded RF choke 30 is replaced by a toroidal shielded RF choke 47 as shown in FIG. 5.

FIGS. 9A and 9B are schematic diagrams of a electrical leads 65A and 65B, respectively, according to still further alternate embodiments of the present invention. As seen in FIG. 9A, the electrical lead 65A includes a plurality of segments of electrical wire 25' which each comprise a multiple conductor wire, preferably in the form of a flexible insulated multiple conductor wire. As noted elsewhere herein, the multiple conductor wire or each conductor therein may be, for example and without limitation, a coaxial wire or a triaxial wire. The electrical lead 65A includes a one or more alternative shielded RF chokes 67A that are preferably spaced at intervals as described above in connection with FIG. 1. As seen in FIG. 9A, each shielded RF choke 67A comprises a layer of shielding material 35 as described above that covers but is not in contact with the conductor portions 75 located between the adjacent segments of electrical wire 25', and a capacitor 70 provided between each such conductor 75 and the layer of shielding material 35. In addition, in the shielded RF choke 67A, an inductor 33 is provided between each conductor 75 and the segment of electrical wire 25' that is electrically upstream (in terms of current flow) from the point at which the capacitor 70 is connected to the conductor 75. In the embodiment shown in FIG. 9A, the capacitors 70 are tuned. The electrical lead 65 B shown in FIG. 9B is similar to the electrical lead 65A, except that in the electrical lead 65B, an inductor 33 is provided between each conductor 75 and the segment of electrical wire 25' that is electrically downstream (in terms of current flow) from the point at which the capacitor 70 is connected to the conductor 75. In the electrical lead 65B, the capacitors 70 are short at relatively high frequencies (on the order of 100 MHz) and therefore no signal is transmitted by the electrical lead 65B, and therefore no signal is provided to the location 20 (such as the brain or some other organ or tissue within the body) shown in FIG. 2. As an alternative, in either electrical lead 65A or 65*b*, the inductors 33 may be wrapped together.

Figure 10:
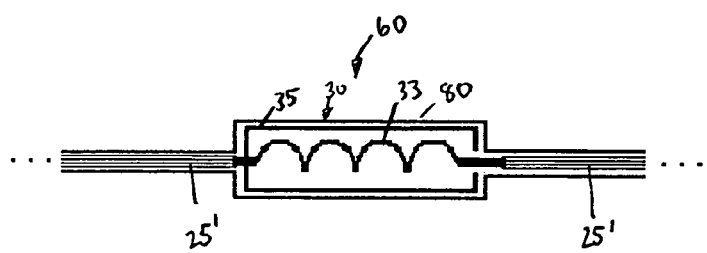

FIG. 10 is a variation of the embodiment shown in FIG. 6 wherein a layer of insulating material 80, such as, without limitation, Teflon, polyethylene, nylon, rubber or pvc, is provided around the segments of electrical wire 25' and the shielded RF chokes 30 except for those areas that must remained exposed for proper operation of the implantable device with which the electrical lead 60 is to be used (as is known, some implantable devices, such as pacemakers, require one or more portions of the leads to be exposed so that an electrical connection or connections to the body can be made). The layer of insulating material 80 will provide further safety as charges may tend to accumulate at the edges of the layer of shielding material 35. The use of the layer of insulating material 80 is not limited to the electrical lead 60, but may also be used with the other embodiments shown herein. In addition, when the electrical lead 60 (or the other electrical leads described herein) are used with an implantable device, the layer of insulating material 80 may also cover the generator 15 (FIG. 2).

Figure 11A:
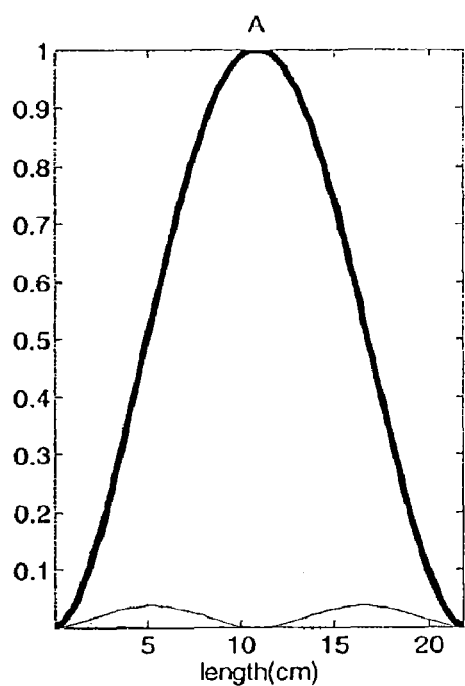
FIG. 11 shows simulation results for electrical lead according to an embodiment of the invention.
Figure 11B:
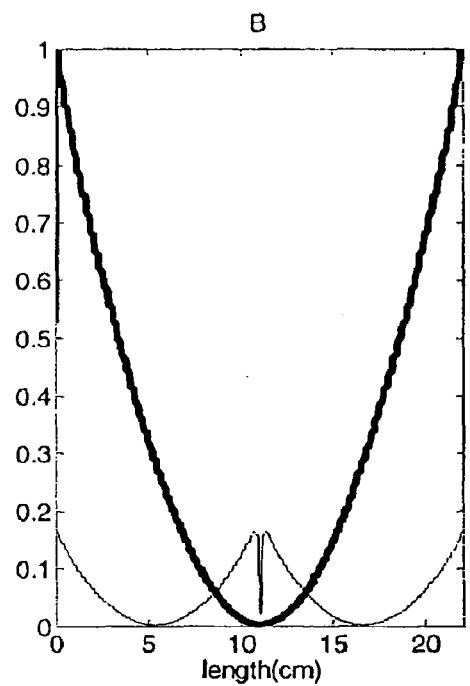

A number of simulations of the performance of the electrical lead 5 were performed by the present inventors. The simulation results are depicted in FIGS. 11A and 11B. FIG. 11A shows the normalized induced current on a regular wire and a lead 5. FIG. 11B shows the SAR distribution on the surface of the regular and the lead 5. From these simulations, it is obvious that the lead 5 is able to separate the wire into two wires.

Figure 12:
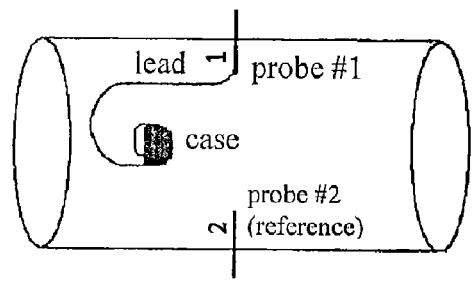
FIG. 12 shows a set up for a gel phantom experiment that was performed on a pacemaker including an electrical lead according to an embodiment of the invention.
Figure 13:
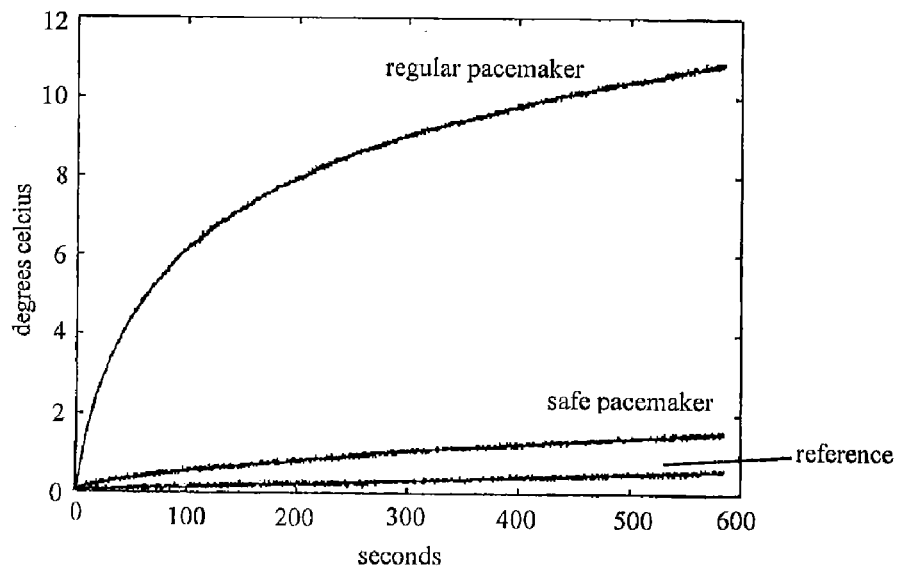
FIG. 13 shows temperature profiles of the gel phantom experiments performed on a pacemaker including an electrical lead according to an embodiment of the invention.

In addition, in order to evaluate the effectiveness of the present invention, gel phantom experiments were performed on a regular pacemaker and a pacemaker including an electrical lead 5. The gel phantom setup is shown in FIG. 12 and includes a temperature probe 1 located at the tip of the pacemaker lead in each case and a reference probe 2. The gel phantom setup for each pacemaker (regular and safe, i.e., including the lead 5) shown in FIG. 12 was subjected to MRI scanning and profiles of the temperatures measured by the probes are shown in FIG. 13. As can be seen, the pacemaker that included the lead 5 experienced significantly less heating.

While preferred embodiments of the invention have been described and illustrated above, it should be understood that these are exemplary of the invention and are not to be considered as limiting. Additions, deletions, substitutions, and other modifications can be made without departing from the spirit or scope of the present invention. Accordingly, the invention is not to be considered as limited by the foregoing description but is only limited by the scope of the appended claims.

What is claimed is:

1. An apparatus that may be implanted within a patient's body which resists the induction of a current from an electromagnetic field external to said apparatus, comprising:
   a generator for generating one or more electrical pulses;
   a lead for delivering the one or more electrical pulses to tissue within the patient's body, said lead including:
   one or more pairs of adjacent segments of electrical wire, each of said pairs including a first segment of electrical wire and a second segment of electrical wire; and
   one or more shielded RF chokes, each of said shielded RF chokes being provided between the first segment of electrical wire and the second segment of electrical wire of a respective one of said one or more pairs of adjacent segments and having a first end operatively coupled to the first segment of electrical wire and a second end operatively coupled to the second segment of electrical wire of the respective one of said one or more pairs of adjacent segments, wherein said one or more pairs of adjacent segments comprises a plurality of pairs of adjacent segments of electrical wire and wherein said one or more shielded RF chokes comprises a plurality of shielded RF chokes.

2. The apparatus according to claim 1, wherein said electromagnetic field includes electromagnetic energy having a first wavelength, and wherein the first segment of electrical wire and the second segment of electrical wire in each of the plurality of pairs of adjacent segments of electrical wire each has a length of no more than about a predetermined percentage of said first wavelength.

3. The apparatus according to claim 2, wherein said predetermined percentage of said first wavelength is twenty five percent.

4. The apparatus according to claim 3, wherein said lead includes a first portion of electrical wire located within said tissue having a length equal to no more than about fifty percent of said first wavelength.

5. The apparatus according to claim 1, wherein each of the adjacent segments of electrical wire is a single conductor electrical wire.

6. The apparatus according to claim 1, wherein each of the adjacent segments of electrical wire is a multiple conductor electrical wire.

7. The apparatus according to claim 1, further comprising a layer of insulating material covering at least a portion of said lead and at least a portion of said generator.

8. The apparatus according to claim 7, wherein said layer of insulating material covers substantially all of said lead except for portions of said lead that must be exposed for proper operation of said apparatus.

9. An apparatus that may be implanted within a patient's body which resists the induction of a current from an electromagnetic field external to said apparatus, comprising:
   a generator for generating one or more electrical pulses;
   a lead for delivering the one or more electrical pulses to tissue within the patient's body, said lead including:
   one or more pairs of adjacent segments of electrical wire, each of said pairs including a first segment of electrical wire and a second segment of electrical wire; and
   one or more shielded RF chokes, each of said shielded RF chokes being provided between the first segment of electrical wire and the second segment of electrical wire of a respective one of said one or more pairs of adjacent segments and having a first end operatively coupled to the first segment of electrical wire and a second end operatively coupled to the second segment of electrical wire of the respective one of said one or more pairs of adjacent segments, wherein one or more of said one or more shielded RF chokes comprises an inductor covered by at least one layer of conductive shielding material.

10. The apparatus according to claim 9, wherein said at least one layer of conductive shielding material comprises two or more layers of conductive shielding material.

11. The apparatus according to claim 9, wherein said at least one layer of conductive shielding material comprises a metallic shielding material.

12. The apparatus according to claim 9, wherein in each case, a first end of the at least one layer of conductive shielding material is electrically connected to the inductor and a second end of the at least one layer of conductive shielding material is either floating or connected to an insulator.

13. An apparatus that may be implanted within a patient's body which resists the induction of a current from an electromagnetic field external to said apparatus, comprising:
   a generator for generating one or more electrical pulses;
   a lead for delivering the one or more electrical pulses to tissue within the patient's body, said lead including:
   one or more pairs of adjacent segments of electrical wire, each of said pairs including a first segment of electrical wire and a second segment of electrical wire; and
   one or more shielded RF chokes, each of said shielded RF chokes being provided between the first segment of electrical wire and the second segment of electrical wire of a respective one of said one or more pairs of adjacent segments and having a first end operatively coupled to the first segment of electrical wire and a second end operatively coupled to the second segment of electrical wire of the respective one of said one or more pairs of adjacent segments, wherein one or more of said one or more shielded RF chokes comprises an inductor covered by at least one layer of conductive shielding material, each said inductor having a core, wherein the core of each said inductor comprises a paramagnetic material.

14. An apparatus that may be implanted within a patient's body which resists the induction of a current from an electromagnetic field external to said apparatus, comprising:
   a generator for generating one or more electrical pulses;
   a lead for delivering the one or more electrical pulses to tissue within the patient's body, said lead including:
   one or more pairs of adjacent segments of electrical wire, each of said pairs including a first segment of electrical wire and a second segment of electrical wire; and
   one or more shielded RF chokes, each of said shielded RF chokes being provided between the first segment of electrical wire and the second segment of electrical wire of a respective one of said one or more pairs of adjacent segments and having a first end operatively coupled to the first segment of electrical wire and a second end operatively coupled to the second segment of electrical wire of the respective one of said one or more pairs of adjacent segments, wherein one or more of said one or more shielded RF chokes comprises a toroidal inductor.

15. The apparatus according to claim 14, wherein said toroidal inductor includes a coil wrapped around a doughnut-shaped core.

16. An apparatus that may be implanted within a patient's body which resists the induction of a current from an electromagnetic field external to said apparatus, comprising:
a generator for generating one or more electrical pulses;
a lead for delivering the one or more electrical pulses to tissue within the patient's body, said lead including:
one or more pairs of adjacent segments of electrical wire, each of said pairs including a first segment of electrical wire and a second segment of electrical wire; and
one or more shielded RF chokes, each of said shielded RF chokes being provided between the first segment of electrical wire and the second segment of electrical wire of a respective one of said one or more pairs of adjacent segments and having a first end operatively coupled to the first segment of electrical wire and a second end operatively coupled to the second segment of electrical wire of the respective one of said one or more pairs of adjacent segments, wherein one or more of said one or more shielded RF chokes comprises a first conductor and a first inductor connected in series and provided between the first segment of electrical wire and the second segment of electrical wire of the respective one of said one or more pairs of adjacent segments, at least one layer of conductive shielding material coveting said first conductor and said first inductor, and a capacitor provided between said first conductor and said at least one layer of conductive shielding material.

17. A method of making an apparatus that may be implanted within a patient's body which resists the induction of a current from an electromagnetic field external to said apparatus, comprising:
providing a generator for generating one or more electrical pulses;
making a lead for delivering the one or more electrical pulses to tissue within the patient's body by (i) providing a plurality of pairs of adjacent segments of electrical wire, each of said pairs including a first segment of electrical wire and a second segment of electrical wire, and (ii) providing a shielded RF choke between the first segment of electrical wire and the second segment of electrical wire of each one of said plurality of pairs of adjacent segments, and operatively coupling said generator to said lead.

18. The method according to claim 17, wherein said electromagnetic field includes electromagnetic energy having a first wavelength, and wherein the first segment of electrical wire and the second segment of electrical wire in each of the plurality of pairs of adjacent segments of electrical wire each has a length of no more than about a predetermined percentage of said first wavelength.

19. The method according to claim 18, wherein said predetermined percentage of said first wavelength is twenty five percent.

20. The method according to claim 17, wherein the step of providing a shielded RF choke comprises providing an inductor between the first segment of electrical wire and the second segment of electrical wire of each one of said plurality of pairs of adjacent segments and covering the inductor with at least one layer of conductive shielding material.

21. The method according, to claim 20, wherein said at least one layer of conductive shielding material comprises two or more layers of conductive shielding material.

22. The method according to claim 20, wherein said at least one layer of conductive shielding material comprises a metallic shielding material.

23. The method according to claim 20, wherein the step of providing a shielded RF choke comprises electrically connecting a first end of the at least one layer of conductive shielding material to the inductor and either allowing a second end of the at least one layer of conductive shielding material to float or connecting the second end of the at least one layer of conductive shielding material to an insulator.

24. The method according to claim 20, wherein each said inductor has a core.

25. The method according to claim 24, wherein the core of each said inductor comprises a paramagnetic material.

26. The method according to claim claim 17, wherein the step of providing a shielded RF choke comprises providing a toroidal inductor between the first segment of electrical wire and the second segment of electrical wire of each one of said one or more pairs of adjacent segments.

27. The method according to claim 26, wherein each said toroidal inductor includes a coil wrapped around a doughnut-shaped core.

28. The method according to claim 17, wherein the step of providing a plurality of pairs of adjacent segments of electrical wire comprises providing a plurality of pairs of adjacent segments of single conductor electrical wire.

29. The method according to claim 17, wherein the step of providing a plurality of pairs of adjacent segments of electrical wire comprises providing a plurality of pairs of adjacent segments of multiple conductor electrical wire.

30. The method according to claim 17, further comprising providing a layer of insulating material over at least a portion of said plurality of pairs of adjacent segments of electrical wire and at least a portion of each shielded RF choke.

31. The method according to claim 30, wherein the step of providing a layer of insulating material further comprises providing a layer of insulating material over at least a portion of said generator.

32. The method according to claim 17, wherein each shielded RF choke comprises a first conductor and a first inductor connected in series and provided between the first segment of electrical wire and the second segment of electrical wire of the respective one of said plurality of pairs of adjacent segments, at least one layer of conductive shielding material covering said first conductor and said first inductor, and a capacitor provided between said first conductor and said at least one layer of conductive shielding material.

* * * * *